(12) United States Patent
Sahatjian

(10) Patent No.: US 6,413,203 B1
(45) Date of Patent: *Jul. 2, 2002

(54) METHOD AND APPARATUS FOR POSITIONING RADIOACTIVE FLUIDS WITHIN A BODY LUMEN

(75) Inventor: Ronald A. Sahatjian, Lexington, MA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/154,267

(22) Filed: Sep. 16, 1998

(51) Int. Cl.⁷ .................................. A61N 5/00
(52) U.S. Cl. .......................................... 600/3
(58) Field of Search .................. 600/1–8; 606/191, 606/192

(56) References Cited

U.S. PATENT DOCUMENTS

| | | |
|---|---|---|
| 2,546,761 A | 3/1951 | Loftus |
| 2,862,108 A | 11/1958 | Meilink |
| 2,955,208 A | 10/1960 | Stevens |
| 3,060,924 A | 10/1962 | Rush |
| 3,147,383 A | 9/1964 | Prest |
| 3,324,847 A | 6/1967 | Zoumboulis |
| 3,505,991 A | 4/1970 | Hellerstein et al. |
| 3,643,096 A | 2/1972 | Jeffries, Jr. et al. |
| 3,669,093 A | 6/1972 | Sauerwein et al. |
| 3,750,653 A | 8/1973 | Simon |

(List continued on next page.)

FOREIGN PATENT DOCUMENTS

| | | |
|---|---|---|
| CA | 2166915 A | 8/1996 |
| DE | G 91 02 312.2 | 8/1992 |
| DE | 195 26 680 A1 | 1/1997 |

(List continued on next page.)

OTHER PUBLICATIONS

Tjho–Heslinga et al., "Results of ruthenium irradiation of uveal melanona", *Radiothereapy Oncology*, vol. 29, pp 33–38, 1993.
Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.
Radiotherapy of Intraoculare and Orbital Tumors, Springer–Verlak publishers, Berlin Heidelberg and New York, copyright 1993, pp. 23–30 and 363–367.
Fackelmann, "Harbinger of a Heart Attack", *Science News*, vol. 151, Jun. 14, 1997, pp. 374–375.
Raloff, "Nuclear Medicine Gets Friendlier—Experimental Therapies Seek to Posion Just the Disease", *Science News*, Bol. 152, Jul. 19, 1997, pp. 40–41.
Sutherland, "Managing Cancer Through Synergy", *Administrative Radiology Journal*, Nov. 1996, pp. 21–27.

Primary Examiner—Samuel G. Gilbert
(74) Attorney, Agent, or Firm—Crompton, Seager & Tufte, LLC

(57) ABSTRACT

A device and method for providing radiation to selected radial portions of a segment of the interior wall of a body lumen. In a preferred embodiment, an intravascular catheter is positioned within a desired blood vessel adjacent to a lesion. A radioactive fluid is then injected into the catheter, and the catheter directs the radioactive fluid about the central axis of the vessel in the area of the lesion. This allows selected radial portions of a vessel to have a higher radiation exposure than other portions, which is particularly useful when a lesion does not uniformly extend around the entire circumference of a vessel.

16 Claims, 2 Drawing Sheets

U.S. PATENT DOCUMENTS

| | | |
|---|---|---|
| 3,811,426 A | 5/1974 | Culver et al. |
| 3,861,380 A | 1/1975 | Chassagne et al. |
| 3,866,050 A | 2/1975 | Whitfield |
| 3,927,325 A | 12/1975 | Hungate et al. |
| 4,096,862 A | 6/1978 | DeLuca |
| 4,220,864 A | 9/1980 | Sauerwein et al. |
| 4,225,790 A | 9/1980 | Parsons, Jr. et al. |
| 4,244,357 A | 1/1981 | Morrison |
| 4,281,252 A | 7/1981 | Parsons, Jr. et al. |
| 4,314,157 A | 2/1982 | Gaines |
| 4,364,376 A | 12/1982 | Bigham |
| 4,584,991 A | 4/1986 | Tokita et al. |
| 4,588,395 A | 5/1986 | Lemelson ............... 604/59 |
| 4,631,415 A | 12/1986 | Sauerwein et al. |
| 4,702,228 A | 10/1987 | Russell, Jr. et al. |
| 4,706,652 A | 11/1987 | Horowitz |
| 4,763,642 A | 8/1988 | Horowitz |
| 4,763,671 A | 8/1988 | Goffinet |
| 4,782,834 A | 11/1988 | Maguire et al. |
| 4,784,116 A | 11/1988 | Russell, Jr. et al. |
| 4,815,449 A | 3/1989 | Horowitz ................. 600/7 |
| 4,819,618 A | 4/1989 | Liprie ..................... 600/7 |
| 4,851,694 A | 7/1989 | Rague et al. ......... 250/497.1 |
| 4,861,520 A | 8/1989 | van't Hooft et al. ...... 252/644 |
| 4,881,937 A | 11/1989 | van't Hooft et al. ........ 600/3 |
| 4,897,076 A | 1/1990 | Puthawala et al. ........... 600/7 |
| 4,936,823 A | 6/1990 | Colvin et al. ............. 600/7 |
| 4,963,128 A | 10/1990 | Daniel et al. ............. 600/7 |
| 4,969,863 A | 11/1990 | van't Hooft et al. ........ 600/3 |
| 4,976,266 A | 12/1990 | Huffman et al. |
| 4,976,680 A | 12/1990 | Hayman et al. ............ 600/7 |
| 4,976,690 A | 12/1990 | Solar et al. ............ 604/96 |
| 5,030,194 A | 7/1991 | Van't Hooft .............. 600/3 |
| 5,032,113 A | 7/1991 | Burns .................. 604/96 |
| 5,059,166 A | 10/1991 | Fischell et al. ............ 600/3 |
| 5,084,001 A | 1/1992 | Van't Hooft et al. ......... 600/3 |
| 5,084,002 A | 1/1992 | Liprie ..................... 600/7 |
| 5,092,834 A | 3/1992 | Bradshaw et al. ........... 600/7 |
| 5,103,395 A | 4/1992 | Spako et al. |
| 5,106,360 A | 4/1992 | Ishiwara et al. ............ 600/2 |
| 5,120,973 A | 6/1992 | Rohe et al. ........... 250/497.1 |
| 5,139,473 A | 8/1992 | Bradshaw et al. ........... 600/3 |
| 5,141,487 A | 8/1992 | Liprie .................... 600/7 |
| 5,147,282 A | 9/1992 | Kan .................... 600/1 |
| 5,163,896 A | 11/1992 | Suthanthiran et al. ........ 600/8 |
| 5,176,617 A | 1/1993 | Fischell et al. ............ 600/3 |
| 5,183,455 A | 2/1993 | Hayman et al. ............ 600/7 |
| 5,199,939 A | 4/1993 | Dake et al. ............... 600/3 |
| 5,213,561 A | 5/1993 | Weinstein et al. ........... 600/7 |
| 5,254,089 A * | 10/1993 | Wang ................... 604/96 |
| 5,267,960 A | 12/1993 | Hayman et al. .......... 604/106 |
| 5,282,781 A | 2/1994 | Liprie ..................... 600/3 |
| 5,302,168 A | 4/1994 | Hess ..................... 600/3 |
| 5,344,383 A | 9/1994 | Liping ................... 600/3 |
| 5,354,257 A | 10/1994 | Roubin et al. ............. 600/7 |
| 5,370,685 A | 12/1994 | Stevens ................. 623/2 |
| 5,391,139 A | 2/1995 | Edmundson ............... 600/7 |
| 5,405,309 A | 4/1995 | Carden, Jr. ............... 600/3 |
| 5,409,015 A | 4/1995 | Palermo ................ 128/772 |
| 5,411,466 A | 5/1995 | Hess ..................... 600/3 |
| 5,425,720 A | 6/1995 | Rogalsky et al. .......... 604/198 |
| 5,429,582 A | 7/1995 | Williams ................. 600/2 |
| 5,484,384 A | 1/1996 | Fearnot .................. 600/3 |
| 5,498,227 A | 3/1996 | Mawad .................. 600/3 |
| 5,503,613 A | 4/1996 | Weinberger ............... 600/3 |
| 5,503,614 A | 4/1996 | Liprie .................... 600/7 |
| 5,532,122 A | 7/1996 | Drukier ................. 435/5 |
| 5,538,494 A | 7/1996 | Matsuda ................. 600/1 |
| 5,540,659 A | 7/1996 | Teirstein ............... 604/104 |
| 5,556,389 A | 9/1996 | Liprie ................. 604/264 |
| 5,575,749 A | 11/1996 | Liprie .................... 600/3 |
| 5,605,530 A | 2/1997 | Fischell et al. ............. 600/3 |
| 5,611,767 A | 3/1997 | Williams ................. 600/2 |
| 5,616,114 A | 4/1997 | Thornton et al. ............ 600/3 |
| 5,618,266 A | 4/1997 | Liprie ................... 604/21 |
| 5,624,372 A | 4/1997 | Liprie .................... 600/3 |
| 5,643,171 A | 7/1997 | Bradshaw et al. ........... 600/1 |
| 5,649,924 A | 7/1997 | Everett et al. ............ 606/15 |
| 5,653,683 A | 8/1997 | D'Andrea ............... 604/21 |
| 5,662,580 A | 9/1997 | Bradshaw et al. ........... 600/3 |
| 5,674,177 A | 10/1997 | Hehrlein et al. ............ 600/3 |
| 5,683,345 A | 11/1997 | Waksman et al. ........... 600/3 |
| 5,688,220 A | 11/1997 | Verin et al. ............... 600/1 |
| 5,707,332 A | 1/1998 | Weinberger ............... 600/3 |
| 5,720,717 A | 2/1998 | D'Andrea ............... 604/21 |
| 5,722,984 A | 3/1998 | Fischell et al. ........... 606/198 |
| 5,728,042 A | 3/1998 | Schwager ................. 600/3 |
| 5,730,698 A | 3/1998 | Fischell et al. ............ 600/3 |
| 5,782,740 A | 7/1998 | Schneiderman ............. 600/1 |
| 5,782,742 A | 7/1998 | Crocker et al. ............. 600/3 |
| 5,792,105 A * | 8/1998 | Lin et al. ............... 604/96 |
| 5,795,286 A | 8/1998 | Fischell et al. ............ 600/3 |
| 5,797,948 A * | 8/1998 | Dunham ............... 606/194 |
| 5,800,333 A | 9/1998 | Liprie .................... 600/3 |
| 5,803,895 A | 9/1998 | Kronholz et al. ........... 600/3 |
| 5,807,231 A | 9/1998 | Liprie .................... 600/3 |
| 5,816,259 A | 10/1998 | Rose .................. 128/898 |
| 5,816,999 A | 10/1998 | Bischoff et al. ............ 600/3 |
| 5,820,553 A | 10/1998 | Hughes ................. 600/426 |
| 5,833,593 A | 11/1998 | Liprie .................... 600/3 |
| 5,840,008 A | 11/1998 | Klein et al. ............... 600/3 |
| 5,840,009 A | 11/1998 | Fischell et al. ............ 600/3 |
| 5,840,064 A | 11/1998 | Liprie ................... 604/96 |
| 5,843,163 A | 12/1998 | Wall |
| 5,851,171 A | 12/1998 | Gasson ................... 600/3 |
| 5,851,172 A | 12/1998 | Bueche et al. ............. 600/7 |
| 5,855,546 A | 1/1999 | Hastings et al. ............ 600/3 |
| 5,857,956 A | 1/1999 | Liprie .................... 600/7 |
| 5,863,284 A | 1/1999 | Klein .................... 600/3 |
| 5,863,285 A | 1/1999 | Coletti ................... 600/3 |
| 5,865,720 A | 2/1999 | Hastings et al. ............ 600/3 |
| 5,871,436 A | 2/1999 | Eury ..................... 600/3 |
| 5,871,437 A | 2/1999 | Alt ...................... 600/3 |
| 5,873,811 A | 2/1999 | Wang et al. ............... 600/5 |
| 5,879,282 A | 3/1999 | Fischell et al. ............ 600/3 |
| 5,882,290 A | 3/1999 | Kume .................... 600/3 |
| 5,882,291 A | 3/1999 | Bradshaw et al. ........... 600/3 |
| 5,891,091 A | 4/1999 | Tierstein ............... 604/104 |
| 5,897,573 A | 4/1999 | Rosenthal et al. .......... 606/224 |
| 5,899,882 A | 5/1999 | Waksman et al. .......... 604/96 |
| 5,899,917 A * | 5/1999 | Edwards et al. ........... 606/195 |
| 5,910,101 A * | 6/1999 | Andrews et al. ............ 600/3 |
| 5,916,143 A * | 6/1999 | Apple et al. ............... 600/3 |

FOREIGN PATENT DOCUMENTS

| | | |
|---|---|---|
| DE | 197 54 870 A1 | 8/1998 |
| DE | 197 24 233 C1 | 12/1998 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 593 136 B1 | 3/1997 |
| EP | 0 778 051 A1 | 6/1997 |
| EP | 0 801 961 A2 | 10/1997 |
| EP | 0 813 894 A2 | 12/1997 |
| EP | 0 629 380 B1 | 7/1998 |
| WO | WO 86/03124 | 6/1986 |

| | | | | | | |
|---|---|---|---|---|---|---|
| WO | WO 93/04735 | 3/1993 | | WO | WO 98/16151 | 4/1998 |
| WO | WO 94/25106 | 11/1994 | | WO | WO 98/20935 | 5/1998 |
| WO | WO 94/26205 | 11/1994 | | WO | WO 98/25674 | 6/1998 |
| WO | WO 95/07732 | 3/1995 | | WO | WO 98/29049 | 7/1998 |
| WO | WO 96/06654 | 3/1996 | | WO | WO 98/30273 | 7/1998 |
| WO | WO 96/10436 | 4/1996 | | WO | WO 98/34681 | 8/1998 |
| WO | WO 96/13303 | 5/1996 | | WO | WO 98/36788 | 8/1998 |
| WO | WO 96/14898 | 5/1996 | | WO | WO 98/36790 | 8/1998 |
| WO | WO 96/17654 | 6/1996 | | WO | WO 98/36796 | 8/1998 |
| WO | WO 96/22121 | 7/1996 | | WO | WO 98/39052 | 9/1998 |
| WO | WO 96/29943 | 10/1996 | | WO | WO 98/39062 | 9/1998 |
| WO | WO 96/40352 | 12/1996 | | WO | WO 98/39063 | 9/1998 |
| WO | WO 97/07740 | 3/1997 | | WO | WO 98/40032 | 9/1998 |
| WO | WO 97/09937 | 3/1997 | | WO | WO 98/46309 | 10/1998 |
| WO | WO 97/18012 | 5/1997 | | WO | WO 98/55179 | 12/1998 |
| WO | WO 97/19706 | 6/1997 | | WO | WO 98/57706 | 12/1998 |
| WO | WO 97/25102 | 7/1997 | | WO | WO 99/01179 | 1/1999 |
| WO | WO 97/25103 | 7/1997 | | WO | WO 99/02219 | 1/1999 |
| WO | WO 97/40889 | 11/1997 | | WO | WO 99/04706 | 2/1999 |
| WO | WO 98/01183 | 1/1998 | | WO | WO 99/04856 | 2/1999 |
| WO | WO 98/01184 | 1/1998 | | WO | WO 99/10045 | 3/1999 |
| WO | WO 98/01185 | 1/1998 | | | | |
| WO | WO 98/01186 | 1/1998 | | | | |
| WO | WO 98/11936 | 3/1998 | | | | |

* cited by examiner

METHOD AND APPARATUS FOR POSITIONING RADIOACTIVE FLUIDS WITHIN A BODY LUMEN

FIELD OF THE INVENTION

The invention relates generally to an intravascular catheter device for providing radiation to the interior walls of a human body lumen. More particularly, the invention relates to a catheter and method of use for selectively delivering radiation to portions of the walls of the human body lumen by distributing radioactive fluid non-uniformly within a catheter.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and catheter, possibly in combination with other intravascular devices. A typical balloon catheter has an elongate shaft with a balloon attached proximate the distal end and a manifold attached proximate the proximal end. In use, the balloon catheter is advanced over the guide wire such that the balloon is positioned across and adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of restenosis is not understood, but is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular treatments, including delivery of radioactive radiation have been proposed as a means to prevent or reduce the effects of restenosis. For example, U.S. Pat. No. 5,199,939 to Dake et al. suggests that intravascular delivery of radiation may inhibit restenosis. Dake et al. suggest delivering radiation within the distal portion of a tubular catheter. Fischell, in the publication EPO 0 593 136 A1, suggest placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance from a point source and inversely with distance from a line source, such sources laying off center near one vessel wall in a lumen may overexpose the nearby wall while underexposing the further away wall.

Bradshaw, in PCT publication WO 94/25106, proposes using an inflatable balloon to center the radiation source wire tip. In PCT publication WO 96/14898, Bradshaw et al. propose use of centering balloons which allow blood perfusion around the balloon during treatment. U.S. Pat. No. 5,540,659 to Tierstein suggests use of a helical centering balloon, attached to a catheter at points about the radiation source to allow perfusion through the balloon, and between the balloon and radiation ribbon source.

Use of continuous centering balloons having a beta radiation source within may significantly attenuate the beta radiation when the balloon is filled with inflation fluid. Further, the balloon may allow the radiation source to "warp" when placed across curved vessel regions, allowing the balloon to bend but having the central radiation source lying in a straight line between the two ends. Segmented centering balloons may improve the warping problem but may also increase beta attenuation by allowing blood to lie or flow between the beta source and vessel walls. Balloons allowing external perfusion in general have the aforementioned beta attenuation problem.

Rather than attempting to center a line or point radiation source using centering balloons or the like, U.S. Pat. No. 5,616,114 to Thornton et al. suggests inflating a balloon with a radioactive fluid. The balloon is inflated until the outer surface of the balloon engages the vessel walls. This inflation process requires a substantial amount of radioactive fluid. In this configuration, the radiation emitted by a portion of the fluid, which is distant from the balloon surface, is attenuated before reaching the vessel walls.

In some cases, it may be desirable to provide non-uniform radiation exposure within a vessel, for example, when a lesion does not uniformly extend around the circumference of the vessel wall. For these cases, it may be advantageous to provide more radiation to some segments of the vessel wall and less radiation to others. What remains to be provided, then, is an improved apparatus and method for delivering radiation non-uniformly to vessel walls.

SUMMARY OF THE INVENTION

The present invention provides devices and methods for providing radiation non-uniformly or to selected areas around the circumference of a segment within a given segment of a human body vessel. This allows selected portions of a vessel within a given segment to have a higher radiation exposure than other portions. As indicated above, this may be advantageous when, for example, a lesion is not uniformly distributed around the circumference of a vessel wall.

In one illustrative embodiment, a catheter is positioned within a desired vessel, across and adjacent to a lesion. A radioactive fluid is then injected into the catheter. The catheter directs the radioactive fluid non-uniformly about the central axis of the vessel in the area of the lesion. In an illustrative embodiment, the radioactive fluid is directed to those portions of the vessel wall that have the lesion present, and away from those portions of the vessel wall that are free from the lesion.

It is recognized that a lesion can extend around the entire circumference of the vessel wall, but may be thicker in one area than in another. Accordingly, it is contemplated that different radioactive fluids may be directed to different portions of a lesion. By providing the proper type of radioactive fluid, a particular lesion may receive the proper radiation exposure, while reducing the exposure to other body tissue. A preferred radiation source is a beta emitter, as beta radiation penetrates only a few millimeters into tissue, rather than through the vessel tissue and into other body tissues as can be the case with gamma emitters. However, other radiation sources may also be used.

The catheter preferably includes a shaft with at least one infusion lumen therein, and a balloon member mounted on the distal end of the shaft. The balloon member preferably includes two or more inflatable channel members. Each of the inflatable channel members form part of the outer surface of the balloon member. Selected inflatable channel members are in fluid communication with the infusion lumen of the shaft. An injecting device is used to inject a radioactive fluid into selected inflatable channel members via the at least one infusion lumen. By aligning the selected inflatable channel members with the lesion, the lesion may receive the proper radiation exposure.

It is also contemplated that the shaft may include a second infusion lumen, and that some of the inflatable channel members may be in fluid communication with the second infusion lumen. By selectively injecting radioactive fluid into the appropriate infusion lumen, the proper inflatable channel members may be inflated to irradiate the corresponding portion of the lesion. It is contemplated that any number of separately filled inflatable channel members may be provided to accommodate a wide variety of lesion configurations.

It is further contemplated that some inflatable channels are designed for delivering therapeutic agents into portions of the lesions. These additional therapeutic agents may aid in the treatment of the lesion, or in counteracting the adverse effects of the radiation. Anti-angiogenic, anti-proliferative or anti-thrombogenic drugs are examples of such additional therapeutic agents. With this embodiment, at least one infusion lumen is included in fluid communication with selected drug delivery channel members on the balloon. These drug delivery channel members allow the drug to diffuse through the wall of the channel to the treatment site. The combination of radiation and drug therapy is believed to provide added benefits.

Alternatively, or in addition to, it is contemplated that different radioactive fluids may be injected into each of the infusion lumens to provide different radiation levels and/or radiation types. For example, the concentration of radioactive isotopes and/or the type of radioactive isotopes may be modified to provide a number of different radioactive fluids. By using more than one radioactive fluid, the inflatable channel members that are associated with one of the infusion lumens may exhibit different radiation characteristics than the inflatable channel members that are associated with another one of the infusion lumens. Finally, it is contemplated that the radioactive fluid may be maintained in each of the infusion lumens for different periods of time. This may provide another degree of flexibility in achieving a desired radiation dosage at a particular location within a vessel.

In a preferred embodiment, each of the inflatable channel members is disposed about the outer surface of a primary balloon. When the primary balloon is inflated, the inflatable channel members move outwardly, and preferably ultimately engage the vessel walls. After the primary balloon is inflated, selected inflatable channel members may be inflated with a radioactive fluid to irradiate the desired portion of a lesion. In preferred embodiments, the tubular member, having the lumen for carrying the radioactive fluid, is shielded so that users are not exposed to radiation over the length of the catheter, nor is the vessel lumen wall irradiated at areas other than the treatment site.

The primary balloon is preferably inflated with a non-radioactive fluid. Because the primary balloon occupies much of the cross-sectional area of the vessel when inflated, the amount of radioactive fluid required to fill the inflatable channel members is reduced relative to simply inflating the primary balloon with a radioactive fluid. Thus, the likelihood that a physician and/or a patient will become exposed to unnecessary radiation may be reduced, and the cost of obtaining and storing the radioactive fluid may likewise be reduced.

It is contemplated that the primary balloon may be of a size and type that can be used to perform an angioplasty procedure. That is, the primary balloon may be sized so that it may be positioned adjacent a restriction within a vessel, and of a type so that the restriction becomes dilated when the primary balloon is inflated. Because the inflatable channel members are preferably disposed about the outer surface of the primary balloon, the lesion at the site of treatment can be irradiated during or immediately after the angioplasty procedure. Alternatively, the primary balloon may be positioned across the treatment site after a conventional angioplasty catheter has been utilized to dilate then withdrawn. In either case, after a desired exposure period, the radioactive fluid may be withdrawn from the inflatable channel members, and the non-radioactive fluid may be withdrawn from the primary balloon. The device may then be withdrawn from the patient to complete the procedure.

DETAILED DESCRIPTION OF THE PREFERRED EMBODIMENTS

Figure 1:
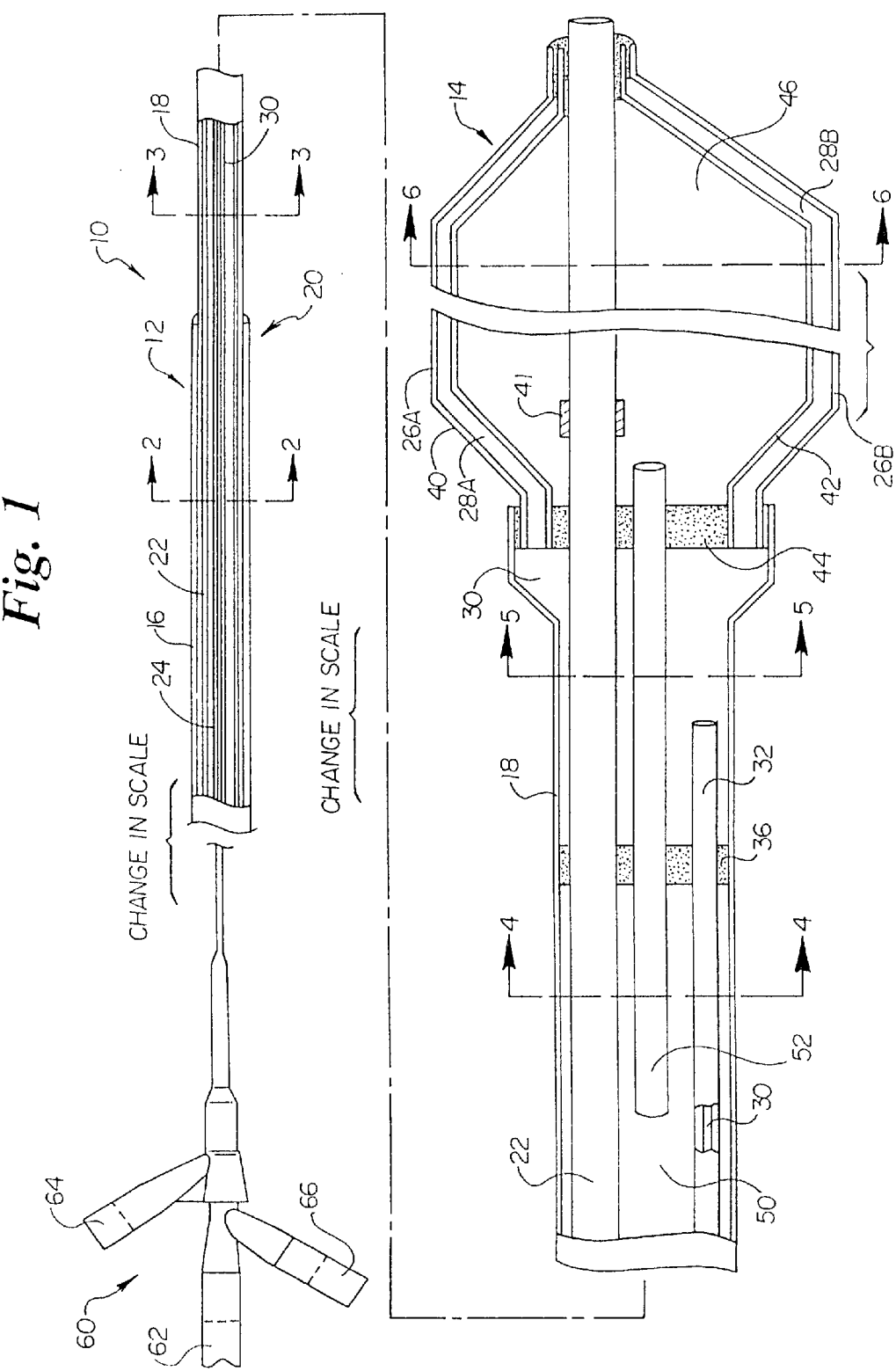
FIG. 1 is a fragmentary side view of a balloon catheter having a channel balloon mounted proximate the distal end thereof.

FIG. 1 is a fragmentary side view of an illustrative balloon catheter 10 in accordance with the present invention. The balloon catheter 10 includes a shaft 12 with a channel balloon 14 mounted proximate the distal end thereof. The shaft 12 includes a proximal outer tube 16 and a distal outer tube 18. The distal outer tube 18 is secured to the proximal outer tube 16 with an adhesive at lap joint 20. To impart more flexibility to the distal portion of the catheter 10, the distal outer tube 16 is preferably more flexible than the proximal outer tube 16. The shaft 12 may further include an inner tube 22 having a guide wire lumen 24 therethrough. A guide wire may be inserted through the guide wire lumen 24 to help guide the catheter 10 to a desired site within the vasculature of a patient. In an illustrative embodiment, the inner tube 22 extends from the proximal end of the catheter 10 to the distal end.

The channel balloon 14 includes two or more channel members. Each channel member includes a chamber for receiving a radioactive fluid. For example, channel member 26A has a chamber 28A and channel member 26B has a chamber 28B. Each chamber is preferably separated from an adjacent chamber via a shared side wall, as more clearly shown in FIG. 6. The channel balloon may be constructed in accordance with U.S. Pat. No. 5,704,912 to Abele et al. and U.S. Pat. No. 5,458,575 to Wang, both disclosures of which are incorporated herein by reference.

In the embodiment of FIG. 1, all of the channel members are inflatable from a single infusion lumen 30. Infusion lumen 30 extends from the proximal end of the catheter 10 to the inflatable chambers, including inflatable chambers 28A and 28B. To reduce the volume of the radioactive fluid that is required to inflate the channel members 26A and 26B, an infusion tube 32 is provided. The infusion tube extends from the proximal end of the catheter 10 to a point just proximal of the channel balloon 14. A first seal 36 is provided to seal the fluid that is provided through infusion tube 32 from flowing proximally into the shaft of the catheter 10. The infusion tube 32 may be shielded to reduce the radiation emitted therefrom.

An outer wall 40 of the channel balloon 14 is attached to the distal outer tube 18, and an inner wall 42 of the channel balloon 14 is attached to a second seal 44. The inner and outer walls, along with the shared side walls, define each of the chambers of channel members 26A and 26B. In this configuration, each chamber of channel members 26A and 26B is in fluid communication with the infusion lumen 30. Although the illustrative embodiment shows for simplicity all of the channel members in fluid communication with a single infusion lumen 30, it is contemplated more than one infusion lumen may be provided so that selected sets or groups of channel members may be separately inflatable via a corresponding infusion lumen.

The distal ends of both the inner wall 42 and outer wall 40 are attached to the inner tube 22 distally of the distal outer tube 18. In this configuration, the inner tube 22 provides longitudinal support to the channel balloon 14, and extends the guide wire lumen 24 to the distal end of the catheter 10. An annular marker band 41 is attached to the inner tube 22 within the channel balloon 14. Using fluoroscopy, the marker band 41 can be used to identify the location of the channel balloon 12 relative to a desired treatment site.

The inner wall 42 of the channel balloon 14 may define a primary balloon having an inner chamber 46. In the illustrative embodiment, the inner chamber 46 is in fluid communication with a primary inflation lumen 50 in combination with a primary inflation tube 52 extending distally therefrom. The primary inflation lumen 50 is formed by the space between the outer tubes 16 and 18, inner tube 22 and infusion tube 32, as more clearly shown in FIGS. 2–3. Primary inflation tube 52 extends proximally of the first seal 36 and distally of the second seal 44, and provides a fluid path between the primary inflation lumen 50 and the inner chamber 46 of the primary balloon.

A manifold 60 is attached proximate the proximal end of the balloon catheter 10. A first access port 62 provides access to the guide wire lumen 24. A second access port 64 provides access to the primary inflation lumen 50. A syringe or the like may be attached to the second access port 64 to inject inflation fluid into the inner chamber 46 of the primary balloon via the primary inflation lumen 50. Preferably, the inflation fluid used to inflate the inner chamber 46 of the primary balloon is non-radioactive. A third access port 66 provides access to the infusion lumen 30. A syringe or the like may be attached to the third access port 66 to inject radioactive fluid into the channel members 26A and 26B via infusion lumen 30.

The manifold, and in particular the third access port 66, may be shielded to reduce the radiation emitted therefrom.

Figure 2:
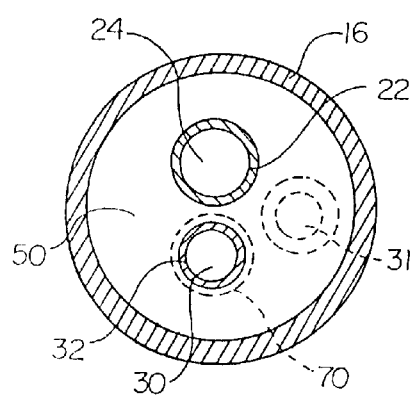
FIG. 2 is a cross-sectional view of the balloon catheter of FIG. 1 taken along line 2—2.

FIG. 2 shows a cross-sectional side view of the balloon catheter 10 of FIG. 1 taken along line 2—2. The proximal outer tube 16 is shown, having inner tube 22 and infusion tube 32 positioned therein. The inner tube 22 defines the guide wire lumen 24. As indicated above, the guide wire lumen 24 preferably extends the entire length of catheter 10. It is contemplated, however, that the guide wire lumen 24 may extend less than the entire length of catheter 10, such as in a monorail or rapid exchange type configuration. The infusion tube 32 defines the infusion lumen 30, which provides a fluid path between the proximal end of the catheter to the appropriate inflatable channel members 26A and 26B. It is contemplated that infusion lumen 30 may have a shield 70 disposed therearound to reduce the radiation emitted therefrom. The space between the proximal outer tube 16, inner tube 22 and infusion tube 32 defines the primary inflation lumen 50.

It is contemplated that the shaft may include a second infusion lumen 31, and that some of the inflatable channel members may be in fluid communication with the second infusion lumen 31. By selectively injecting radioactive fluid into the appropriate infusion lumen, the proper inflatable channel members may be inflated to irradiate the corresponding portion of the lesion. It is contemplated that any number of separately filled inflatable channel members may be provided to accommodate a wide variety of lesion configurations.

It is further contemplated that additional therapeutic agents may be injected into a select infusion lumen which is in fluid communication with drug delivery channel members on the balloon. These drug delivery channels are porous or allow diffusion of a drug through the channel member wall to the treatment site to provide drugs to portions of the lesion. These additional therapeutic agents may aid in the treatment of the lesion, or in counteracting the adverse effects of the radiation. With the addition of these therapeutic agents, physicians may design treatments for a particular lesion. Anti-angiogenic, anti-proliferative or anti-thrombogenic drugs may be incorporated into such treatments. The combination of drugs and radiation is believed to enhance the overall treatment.

Alternatively, or in addition to, it is contemplated that different radioactive fluids may be injected into each of the infusion lumens to provide different radiation levels and/or radiation types. For example, the concentration of radioactive isotopes and/or the type of radioactive isotopes may be modified to provide a number of different radioactive fluids. It is contemplated that the radioactive fluids may be liquid, gas or a solid suspended in a carrier. By using more than one radioactive fluid, the inflatable channel members that are associated with one of the infusion lumens may exhibit different radiation characteristics than the inflatable channel members that are associated with another one of the infusion lumens. Finally, it is contemplated that the radioactive fluid may be maintained in selected infusion lumens for different periods of time. This may provide another degree of flexibility in achieving a desired radiation dosage at a particular location within a vessel.

Figure 3:
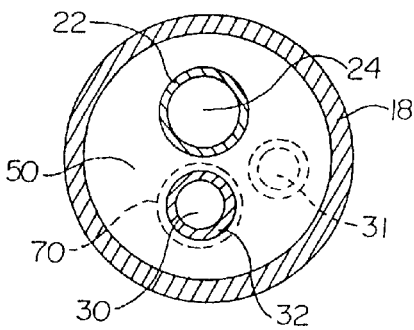
FIG. 3 is a cross-sectional view of the balloon catheter of FIG. 1 taken along line 3—3.
Figure 4:
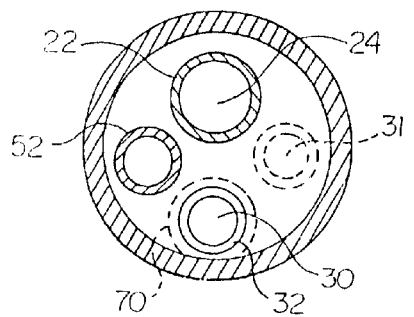
FIG. 4 is a cross-sectional view of the balloon catheter of FIG. 1 taken along line 4—4.

FIG. 3 is a cross-sectional side view of the balloon catheter of FIG. 1 taken along line 3—3. FIG. 3 is similar to that shown in FIG. 2, but shows the distal outer tube 18 disposed around the inner tube 22 and the infusion tube 32, rather than the proximal outer tube 16. FIG. 4 is a cross-sectional side view of the balloon catheter of FIG. 1 taken along line 4—4. FIG. 4 is similar to that shown in FIG. 3, but further shows a proximal portion of the primary inflation tube 52. As indicated above, the primary inflation tube 52 provides a fluid path between the primary inflation lumen 50 and the inner chamber 46 of the primary balloon.

Figure 5:
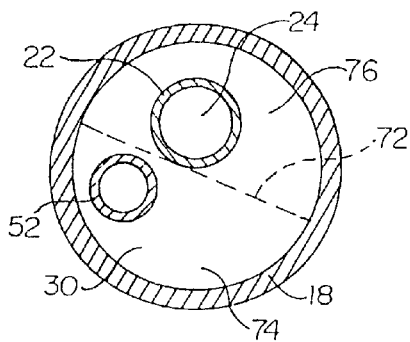
FIG. 5 is a cross-sectional view of the balloon catheter of FIG. 1 taken along line 5—5.

FIG. 5 is a cross-sectional side view of the balloon catheter of FIG. 1 taken along line 5—5. FIG. 5 is similar to that shown in FIG. 4. However, because line 5—5 crosses catheter 10 distally of the infusion tube 32, infusion tube 32 is not shown. The infusion lumen 30 continues, however, via the space between the distal outer tube 18, the inner tube 22 and the primary inflation tube 52. In this illustrative embodiment, all of the inflatable channel members 26A and 26B are in fluid communication with infusion lumen 30. Thus, the space between the distal outer tube 18, the inner tube 22 and the primary inflation tube 52 provides the fluid path between the infusion tube 32 and the chambers of each of the inflatable channel members 26A and 26B.

As indicated above, it is contemplated that more than one infusion lumen may be provided so that selected sets or groups of channel members may be separately inflatable via a corresponding infusion lumen. This may be accomplished by, for example, providing two or more infusion tubes that extend from the proximal end of catheter 10 to a point distally of the first seal 36 but proximally of the second seal 44. The area between the first seal 36 and the second seal 44 may then be divided into a corresponding number of regions by one or more walls. An illustrative wall 72 is shown in FIG. 5. The wall 72 would be constructed such that the first region 74 would be in fluid communication with a first group of inflatable channel members and the second region 76 would be in fluid communication with a second group of inflatable channel members.

Figure 6:
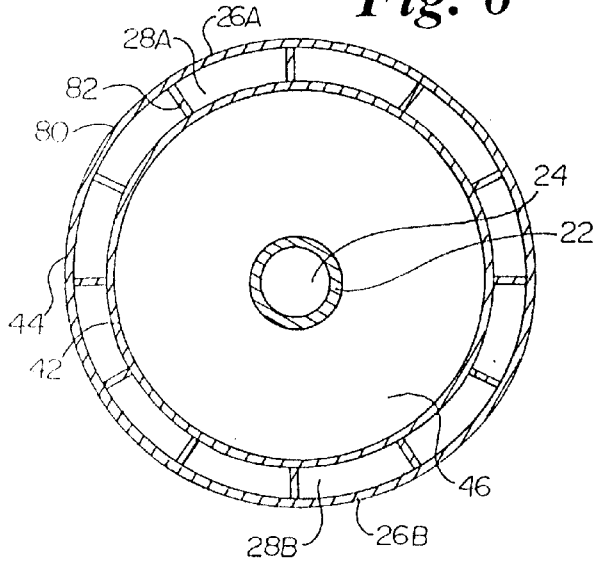
FIG. 6 is a cross-sectional view of the balloon catheter of FIG. 1 taken along line 6—6 showing the channels within the balloon.

FIG. 6 is a cross-sectional side view of the balloon catheter of FIG. 1 taken along line 6—6. FIG. 6 shows a number of inflatable channel members extending circumferentially around the inner tube 22. Each of the inflatable channel members defines a chamber. For example, channel member 26A defines chamber 28A. Preferably, each channel member shares a common side wall with an adjacent channel member. For example, channel member 26A shares a common side wall 82 with adjacent channel member 80.

Each of the inflatable channel members is disposed about the surface of a primary balloon. In the embodiment shown, the inner surface 42 forms the outer surface of the primary balloon. When the primary balloon is inflated, the inflatable channel members move outwardly, and preferably ultimately engage a vessel wall. After the primary balloon is inflated, selected inflatable channel members may be inflated with a radioactive fluid to irradiate the desired portion of a lesion.

As indicated above, the primary balloon is preferably inflated with a non-radioactive fluid. Because the primary balloon occupies much of the cross-sectional area of the vessel when inflated, the amount of radioactive fluid required to fill the inflatable channel members is reduced relative to simply inflating the primary balloon with a radioactive fluid. Thus, the likelihood that a physician and/or a patient will become exposed to unnecessary radiation may be reduced, and the cost of obtaining and storing the radioactive fluid may likewise be reduced.

It is contemplated that the primary balloon may be of a size and type that can be used to perform an angioplasty procedure. That is, the primary balloon may be sized so that it may be positioned adjacent a restriction within a vessel, and of a type so that the restriction becomes dilated when the primary balloon is inflated. Because the inflatable channel members are preferably disposed about the outer surface of the primary balloon, the lesion at the site of treatment can be irradiated during or immediately after the angioplasty procedure. Alternatively, the primary balloon may be positioned across the treatment site after a conventional angioplasty catheter has been withdrawn. In either case, after a desired exposure period, the radioactive fluid is withdrawn from the inflatable channel members, and the non-radioactive fluid is withdrawn from the primary balloon. The device may then be withdrawn from the patient to complete the procedure.

Figure 7:
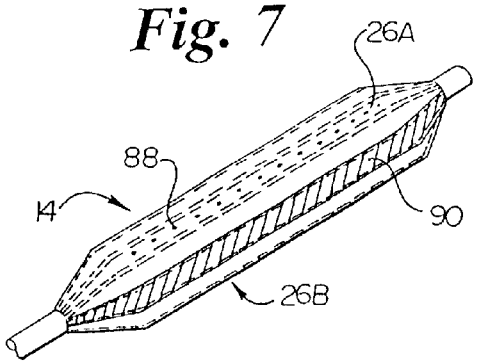
FIG. 7 is a perspective view of an alternative balloon having a larger number of channels therein.

FIG. 7 is a perspective view of an alternative channel balloon having a larger number of channel members, including channel members 26A and 26B. Each of the channel members extends from the proximal end of the channel balloon 14 to the distal end thereof. As described above, the channels can be selectively filled with radioactive fluid. In an alternative embodiment, it is contemplated that selected channel members may have a number of perfusion holes 88 therein for delivering radioactive seeds or additional therapeutic agents as described herein into the vessel walls, if desired. Further, it is contemplated that the outer surface 44 of the channel members may be coated with a drug release coating having a therapeutic substance therein. Finally, it is contemplated that at least some of the channel members may have a shield 90 placed thereover. The shield 90 may be formed from metal or the like, and may reduce the radiation emitted from the channel members thereunder. The shield 90 may allow all channel members to be inflated with a radioactive fluid, while still providing a non-uniform radiation pattern to the vessel wall.

In another alternative embodiment, the catheter balloon of the present invention could be used with radioactive material within the primary balloon and selectively filling certain channels of the balloon with a radiation shielding or absorbing liquid. Selected portions around the circumference could be treated in this manner.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is defined in the language in which the appended claims are expressed.

What is claimed is:

1. A catheter for providing localized radiotherapy to a vascular wall defining a vascular lumen, the catheter comprising:
   a shaft having an inflation lumen and a separate injection lumen;
   an injecting means for injecting a radioactive fluid into the injection lumen of the shaft;
   a directing means for directing the radioactive fluid adjacent the vascular wall, the directing means defining a plurality of channels sharing a common wall with adjacent channels and sealed from the vascular lumen and the inflation lumen; and
   an inflation means for radially displacing the directing means, the inflation means being in fluid communication with the inflation lumen.

2. A catheter according to claim 1 wherein the directing means further directs the radioactive fluid non-symmetrically about the central axis of the shaft.

3. A catheter for insertion into a body conduit, the catheter comprising:
   a shaft having an inflation lumen and a separate injection lumen;
   a balloon member with an outer surface having a plurality of channel members sharing a common wall with adjacent channel members and sealed from the body conduit, wherein the balloon member is in fluid communication with the inflation lumen and the channel members are in fluid communication with the injection lumen; and
   an injection apparatus for injecting a radioactive material into the channel members via the injection lumen.

4. A catheter according to claim 3 wherein the channel members are positioned radially about the shaft.

5. A catheter according to claim 4 wherein selected channel members share a conunon wall with adjacent channel members.

6. A catheter according to claim 3 wherein the shaft includes a first and a second injection lumen with a first set of the channel members in fluid communication with the first infection lumen and a second set of the channel members in fluid communication with the second injection lumen.

7. A catheter according to claim 6 further comprising a a therapeutic agent injection apparatus for injecting a therapeutic agent into the second set of channel members.

8. A catheter according to claim 7 wherein the therapeutic agent is selected from the group consisting of an antiangiogenic agent, anti-proliferative agent, anti-thrombogenic agent, and a drug which alleviates the undesirable effects of radiation and works in concert therewith.

9. A catheter according to claim 3 wherein the radioactive material is a liquid.

10. A catheter according to claim 3 wherein the radioactive material is a gas.

11. A catheter according to claim 3 wherein the radioactive material is a solid in a fluid carrier.

12. A catheter according to claim 3 wherein the shaft has a guide wire lumen extending at least partially therethrough.

13. A catheter according to claim 3 wherein the injection lumen is formed with a shielded tubular member to prevent radiation exposure outside the injection lumen.

14. A method of localized radiotherapy of a selected portion of a vascular wall defining a vascular lumen in a patient, the method comprising the steps of:

providing a catheter including an elongated shaft having an inflation lumen and a separate injection lumen, a balloon disposed about a distal portion of the shaft, the balloon having a plurality of channel members disposed about an outer surface of the balloon member, the channel members being in fluid communication with the injection lumen and sealed from the vascular lumen wherein the balloon includes a first and a second set of channel members;

advancing the catheter through the vascular lumen of the patient until the balloon member is disposed adjacent the selected portion;

inflating the balloon via the inflation lumen; and injecting a radioactive fluid into the channel members via the injection lumen.

15. A method according to claim 14, further comprising the step of injecting a radioactive fluid into the first and second sets of the channel members.

16. A method according to claim 14, further comprising the step of injecting a radioactive fluid into the first set of channel members and injecting a non-radioactive fluid into the second set of channel members.

* * * * *